United States Patent
Itai et al.

(10) Patent No.: US 6,549,900 B2
(45) Date of Patent: Apr. 15, 2003

(54) METHOD FOR CREATING PHYSIOLOGICALLY ACTIVE COMPOUNDS

(75) Inventors: Akiko Itai, 5-16-6, Hongo, Bunkyo-ku, Tokyo (JP), 113-0033; Koichi Shudo, Tokyo (JP)

(73) Assignee: Akiko Itai, Tokyo (JP)

( * ) Notice: Subject to any disclaimer, the term of this patent is extended or adjusted under 35 U.S.C. 154(b) by 0 days.

(21) Appl. No.: 09/816,658

(22) Filed: Mar. 26, 2001

(65) Prior Publication Data

US 2002/0062155 A1 May 23, 2002

Related U.S. Application Data

(63) Continuation of application No. 09/091,837, filed as application No. PCT/JP96/03866 on Dec. 17, 1996, now abandoned.

(30) Foreign Application Priority Data

Dec. 28, 1995 (JP) ............................................. 7-342488

(51) Int. Cl.[7] .......................... G06F 17/30; G06F 19/00; G01N 33/50
(52) U.S. Cl. ............................................ 707/6; 702/27
(58) Field of Search ....................... 707/104, 6; 702/27, 702/19, 22; 435/6, 7.1

(56) References Cited

U.S. PATENT DOCUMENTS 5,642,292 A    6/1997    Itai et al.

FOREIGN PATENT DOCUMENTS

| EP | 0633534 | 1/1995 |
| JP | 6-309385 | 5/1994 |
| JP | 7-133233 | 3/1995 |
| WO | 93/20525 | 10/1993 |
| WO | 96/13785 | 5/1996 |
| WO | 97/18180 | 5/1997 |

OTHER PUBLICATIONS

Nishibata et al., *Tetrahedron*, vol. 47, pp. 8985–8990 (1991).
Nishibata et al., *J. Med. Chem.*, vol. 36, pp. 2921–2928 (1993).
Yamada et al., *J. Mol. Biol.*, vol. 243, pp. 310–326 (1994).
Mizutani et al., 24th Symposium for Structure Activity Relationship, Subject No. 14S20 (1996).
Gallop et al., *J. Med. Chem.*, vol. 37, pp. 1233–1251 (1994).
Burgess et al., *J. Med. Chem.*, vol. 37, pp. 2985–2987 (1994).
Sadowski et al., *J. Chem. Rev.*, vol. 93, pp. 2567–2481 (1993).
Weiner et al., *J. Am. Chem Soc.*, vol. 106, pp. 765–784 (1984).
Tomioka, *J. of Computer–Aided Molecular Design*, vol. 1, pp. 197–210 (1987).
Warshel, *J. Phys. Chem.*, vol. 83, pp. 1640–1652 (1979).
Fletcher et al., *Computer Journal*, vol. 6, pp. 163 (1968).
Kabsch, *Acta. Cryst.*, A32, pp. 922 (1976).
Kabsch, *Acta. Cryst.*, A34, pp. 827 (1978).
Desjarlais et al., *J. Med. Chem.* 31, pp. 722–729 (1989).
Lam et al. *Science* 263, pp. 380–384 (1994).

(List continued on next page.)

*Primary Examiner*—Jack M Choules
(74) *Attorney, Agent, or Firm*—Greenblum & Bernstein, P.L.C.

(57) ABSTRACT

A method for creating physiologically active compounds, comprising the following steps: (1) generating a compound database storing molecular structures covering all the combinations of at least one substitution site selected from substitutable sites existing on a basic molecular skeleton and utilizable substituents; and (2) extracting molecular structures satisfying requirements for exhibiting the physiological activity from the compound database.

18 Claims, 1 Drawing Sheet

OTHER PUBLICATIONS

Miller et al. *Journal of Computer–Aided Molecular Design* 8, pp. 153–174 (1994).
Mizutani et al. *J. Mol. Biol.* 243, pp. 310–326 (1994).
Yamada and Itai *Chem. Pharm. Bull.* 41 (6), pp. 1200–1202 (1993).
Yamada and Itai *Chem. Pharm. Bull.* 41 (6), pp. 1203–1205 (1993).
Martin, Yvonne C., Database accension No.: 114:80616 CA XP002196005.
Moon, J., and Howe, W., Proteins:, Struct., Funct., Genet. 11(4), pp. 314–328 (1991).
Boehm, Hans J., Database accenssion No.: 119:66291 CA XP002196006.
Boehm, Hans J., J. Computer–Aided Mol. Des. 6, pp. 61–78 (1992).
Desjarlais et al., *Proc. Natl. Acad. Sci.*, USA, vol. 87, pp. 6644–6648, 1990.
Moon et al., *Tetrahedron Computer Methodology*, vol. 3, No. 6C, pp. 697–711, 1990.
Saito et al., *Experimental Medicine*, vol. 12, No. 4 (Mar. Issue), pp. 68 (444)–70(446), 1994.
Itai,et al., Structural Analysis of Malarial DHFR and Inhibitor Design, Report in Fiscal Year Heisei 6 (Mar. 1995) on "Chemistry of Natural Super Molecules" in the intensive field research made by a subsidy of the Ministry of Education, Mar. 1995, pp. 212–215.
Boehm, *Journal of Computer–Aided Molecular Design*, 6(1992)593–606.
Pearlman et al., *J. Of Comp.Chem.*, vol. 14, No. 10, pp. 1184–1193, 1993.
Gehlhaar et al., *J. Med. Chem.*, vol. 38, pp. 466–472, 1995.
Boehm, *Journal of Computer–Aided Molecular Design*, 6(1992) 61–78.
Rotstein et al., *J. Med. Chem.*, vol. 36, pp. 1700–1710, 1993.
Gillet et al, *Journal of Computer–Aided Molecular Design*, 7(1993)127–153.
Eisen et al., *Proteins: Structure, Function, and Genetics*, 19:199–221 (1994).
Inoue et al., "The 19th Symposium for Structure–Activity Relationship", subject number 29S23, 1991, including pp. 316–319 and p. 372 with English abstract.
Kanazawa et al. "The 20th Symposium for Structure–Activity Relationship" subject number 27S22, 1992, including pp. 258–261 and p. 322 with English abstract.
Takeda et al. "The 21st Symposium for Structure–Activity Relationship", subject number 26S25, 1993, including pp. 321–324 including English Abstract on p. 324.
Ullman. *J. Assoc. Comput. Mach.*, vol. 23, p. 31, 1976.
Sadowski et al. *Chem. Rev.*, vol. 93, pp. 2567–2581, 1993.
Tomoika et al. *J. Comput Aided Mol. Design*, vol. 8, p. 347, 1994.
Kato et al. *Tetrahedron Lett.*, vol. 43, pp. 5229–5236, 1987.
Itai et al. "Molecular Symposium for Rational Drug Design" in 3DQSAR in Drug Design Theory, Methods and Applications, Ed. Kubinyi, H. EsCOM, Netherland, pp. 200–225, 1993.
Bolin. *J. Biol. Chem.*, vol. 257, p. 13650, 1982.

FIGURE 1

METHOD FOR CREATING PHYSIOLOGICALLY ACTIVE COMPOUNDS

CROSS REFERENCE TO RELATED APPLICATION

This application is a continuation of application Ser. No. 09/091,837, filed Jul. 13, 1998, now abandoned, which is the National Stage of International Application No. PCT/JP96/03866 filed Dec. 17, 1996, published in the Japanese language, and claims priority of Japanese Application No. 7/342488 filed Dec. 28, 1995. The entire disclosure of application Ser. No. 09/091,837 is considered as being part of the disclosure of this application, and the entire disclosure of application Ser. No. 09/091,837 is expressly incorporated by reference herein in its entirety.

TECHNICAL FIELD

The present invention relates to a method for creating physiologically active compounds useful for drugs, agricultural chemicals and the like by using computers.

BACKGROUND ART

In order to create useful drugs, agricultural chemicals and the like, it is essential to use a lead compound that has been already confirmed to have a desired physiological activity which should be a starting point of various chemical modifications. However, any logical method for creating a lead compound has not yet been known. Therefore, in general, physiologically active substances, e.g., hormones or nerve transmitter substances in a living body, or compounds that have already been confirmed to have a desired physiological activity by random screening are used as lead compounds.

On the other hand, three-dimensional structures of a lot of biopolymers have been already elucidated by X-ray crystallography, and many three-dimensional structures of complexes of a low molecular weight compound (ligand) such as an enzyme inhibitor and a biopolymer have also been reported. As a result, it has been revealed a natural rule that, in order to have a physiological activity, it is essential for a compound to fit the binding site of the biopolymer with good fitness and able to stably bind thereto. On the basis of these findings, it becomes possible to determine whether or not a compound exhibits physiological activity through binding to the biopolymer, i.e., whether or not the compound may possibly act as a ligand, by calculating the possibility of binding to the ligand binding site of the target biopolymer and the compound, strength of the binding and the like by means of computers. This method is paid much attention as means for rationally generating lead compounds, physiologically active compounds and the like.

As computersized methods for creating physiologically active compounds, there have been known a method of automatically constructing structures that are able to bind to the ligand-binding site of the biopolymer in an optimal condition (e.g., a condition that affords maximum hydrogen bond) by computation (automatic structure construction method), and a method of identifying compounds that satisfy requirements for having the physiological activity from databases of existing compounds (database method).

As the automatic structure construction method, the method of Nisibata et al. has been known (Nishibata, Y. and Itai, A, Tetrahedron, 47, pp.8985–8990, 1991; Nishibata, Y and Itai, A, J. Med. Chem, 36, pp.2921–2928, 1993). The advantage of the automatic structure construction method is that it can broadly suggest desirable structures that meet the requirements for exhibiting physiological activity regardless of known or unknown structures.

As the database method, there has been known a method of selecting compounds by judging whether or not types of functional groups, their relative three-dimensional positions and other in compounds correspond to those in a drug already known to bind to a biopolymer based on the structural information of the drug (for example, a method utilizing programs such as ISIS-3D:MDL Information Systems, Inc.; UNITY: Tripos, Inc.; and Chem-X: Chemical Design Ltd). This method can be utilized even when structural information of the target biopolymer is not available, and therefore, it can be used for a wide range of purposes.

When three-dimensional coordinates of the ligand-binding region of biopolymers are available, a more reliable database search method excluding any hypotheses and preconceptions can be utilized. The present inventors developed a method for automatically estimating the most stable complex structure of a biopolymer and a ligand (program "ADAM", PCT International Publication WO93/20525; Yamada, M. et al., J. Mol. Biol., 243, pp.310–326, 1994), and, by using this method, completed a method for identifying ligand compounds capable of stably binding to the ligand-binding region of a target biopolymer from a three-dimensional structure database (program "ADAM&EVE", PCT International Publication WO96/13785; the 24th Symposium for Structure-Activity Relationship, Mizutani M et al., subject number 14S20, 1996). This method is characterized in that it enables high speed search of desired ligand compounds from a database based on energetic stability of complexes while not only considering degrees of freedom for binding modes and conformations but also optimizing torsion angles in a continuous space.

When the basic molecular skeleton of a ligand structure that has been confirmed or assumed to bind to the target biopolymer is available, a high-speed database search method based on the matching of topologies can be utilized program "EUREKA", PCT/JP96/03325). In this method, derivatives that can bind to the ligand-binding region of the biopolymer or molecules having analogous structures (analogs) can be retrieved from a database based on the binding mode to the biopolymer and conformations of the basic molecular skeleton.

While the above database search method may be applied to a database composed of any compounds, it has an advantage that, by searching a database of available (in-house or commercially available) compounds, one can immediately obtain hit compounds satisfying the requirements and evaluate their biological activity without syntheses. When a database storing only existing (reported) compounds is used, the method has an advantage that the identified compounds may at least exist, and synthetic method and physicochemical properties thereof are often already known, although the compounds might not be immediately obtained without synthesis.

However, structures stored in such databases of available compounds or existing compounds constitute only a part of an astronomical number of structures that can theoretically exist, and the structures may sometimes be biased or they may exist sparsely among the possible structures. Therefore, they often do not contain any compounds with an optimum chemical structure endowing the maximum physiological activity in nature. When such a database is used and if retrieved compounds have physiological activity, there arise problems that truly promising compounds as lead compounds may be overlooked because of a weak activity of retrieved compounds, and that great effort and time may be needed for improving the retrieved compounds because of large deviation from the optimal structure.

When a certain structure has been known as a lead, or alternatively, a lead has been found by random screening or the aforementioned methods, improvement to achieve the highest desired physiological activity by chemical modification is conventionally performed by synthesizing a great number of derivatives and analogous compounds by trial-and-error, and therefore, it requires great efforts and time.

On the other hand, as an experimental method for efficient development of medicaments, a method comprising simultaneous synthesis or parallel screening of a large number of compounds consisting of those covering all possibilities of functional groups in natures and positions and structural units in connecting order and the like attracts much attention (combinatorial method). For example, a large number of compounds covering all combinations of substitutable positions present on a basic molecular skeleton and substituents, or all combinations of connecting order of two or more structural units like peptides are first generated, synthesized by parallel operations of several steps, and subjected all the compounds to an assay for the physiological activity at a time (Gallop, M A et al., J. Med. Chem., 37, pp.1233–1251, 1994: Burgess, K et al., J. Med. Chem., 37, pp.2985–2987, 1994). This method has an advantage that lead generation and optimization of the physiological activity can be done by the same procedure, because the most physiologically active compound with the basic molecular skeleton is readily selected from the generated combinations.

DISCLOSURE OF THE INVENTION

An object of the present invention is to provide a method for efficiently creating physiologically active compounds, wherein the aforementioned problems are solved by use of computers. More specifically, the object of the present invention is to identify compounds having structures suitable for the desired physiological activity through appropriate selection from generated compounds covering all possibilities in types or positions of functional groups to be added to a basic molecular skeleton, or in connecting order of various structural units.

The present inventors conducted various studies to develop a method for directly identifying an optimal structure as favorable as possible for a desired physiological activity without great trial-and-error efforts, and as a result, achieved the above object by combining a database construction method based on the concept of the above mentioned experimental combinatorial method and the database search method that has been developed by the present inventors. That is, the present inventors found that extremely efficient creation of physiologically active compounds can be performed by generating three-dimensional struck databases of compounds covering at combinations of substitutable positions and substituents for various basic molecular skeletons, or combinations of connecting order of structural units by computers, and searching the database by the above mentioned database search method. Because it becomes possible by employing this method to search a database containing an enormous number of compounds, which is completely impossible to be realized by the conventional combinatorial method utilizing chemical syntheses, compounds that may exhibit the maximum physiological activity can be identified by a single search. The present invention has been completed based on these findings.

The present invention thus provides a method for creating physiologically active compounds using computers, comprising the following steps: (1) generating a compound database storing molecular structures covering all the combinations of one or more substitution site selected from substitutable sites existing on a basic molecular skeleton and utilizable substituents; and (2) idetifying a molecular structure satisfying the requirements necessary for exhibiting the physiological activity from the compound database. As used herein, the term "generation of physiological activity compound" should be construed to have its broadest meaning including concepts of creation and optimization of compounds having physiological activity such as creation of novel lead compounds, creation of novel lead compounds and optimization of the created lead compounds, and optimization of novel lead compounds utilizing molecular skeletons of already known ligand compounds.

In the step (1), any basic molecular skeletons may be used so long as structural modifications such as replacement, addition, or removal of substituents are possible. However, it is preferred to use the whole or a part of the basic structure of a ligand that has been already confirmed or is expected to have the desired biological activity, or a molecular structure which is not difficult to be synthesized or synthetically modified in its structure. Examples of the basic structure that has been already confirmed to have desired biological activity include benzodiazepine skeleton, barbiturate skeleton and the like. Examples of the basic structure that is expected to have the desired biological activity include those molecular structures created or selected by the methods utilizing "LEGEND" or "ADAM&EVE". Examples of the molecular structure easy to be synthesized or synthetically modified in its structure include molecular skeletons created by connecting one or more structural units having modifiable sites and one or more connectors alternately. In this case, the basic molecular skeleton may be suitably selected from one or more molecular skeletons combinatorially generated from combinations of one or more structural units and connectors.

According to other embodiments of the present invention, there are provided three-dimensional databases used for the method of creating physiologically active compounds by database search methods using computers, which database stores molecular structures covering all the combinations of one or more substitution sites selected from substitutable sites existing on a basic molecular skeleton and utilizable substituents; and computer-readable media storing the database. The basic molecular skeleton used for generating molecular structures stored in the database may be any molecular skeletons for which structural modifications such as replacement, addition, or removal of substituents are possible. Specifically, those mentioned above can be used.

BEST MODE FOR CARRYING OUT THE INVENTION

The first step of the method of the present invention comprises covering all the combinations of one or more substitution sites selected from substitutable sites existing on a basic molecular skeleton and utilizable substituents by using computers, creating all molecular structures possible for the basic molecular skeleton, and storing the created molecular structures in a database. If necessary, conditions for combinations may be preliminarily established, and molecular structures are generated based on all the combinations acceptable under the conditions in order to effectively utilize computer resources. The method of the present invention is characterized in that molecular structures satisfying the requirements necessary for exhibiting the physiological activity are identified from the exhaustive combinatorial compound database obtained by the above step (second step).

The generation of molecular structures to be stored in databases may be performed by, for example, the following steps:

(A) step of selecting one or more basic molecular skeletons on which molecular structures are generated from molecular skeletons of known compounds or their analogous molecular skeletons, or generating them by combination;

(B) step of selecting one or more substitution sites to which substituents are introduced from one or more substitutable sites existing on the basic molecular skeletons for each basic molecular skeleton;

(C) step of nominating utilizable substituents, and if necessary, determining a maximum use of each nominated substituent, or corresponding the substituents to each substitution site; and (D) preparing all the possible combinations of all the substitution sites selected in the above step (B) and all the substituents nominated in the above step (C), or when an optional condition is established in the above step (C), preparing all the possible combinations satisfying the condition to generate molecular structures of compounds.

In the step (A), the basic molecular skeletons can be suitably selected from basic structures of known ligands having a desired biological activity, for example, those already available for those skilled in the art as basic molecular structures for drugs, agricultural chemicals and the like, such as benzodiazepine skeleton, barbiturate skeleton, urea skeleton, phenothiazine skeleton, butyrophenone skeleton, xanthine skeleton, phenethylamine skeleton, morphine skeleton, prostaglandin skeleton, steroid skeleton, penicillin skeleton, cephalosporin skeleton, quinolonecarboxylic acid skeleton, tetracycline skeleton and analogous molecular skeletons thereof, for example, homologues thereof.

In the step (A), the basic molecular skeleton itself may also be generated by combination. For this purpose, for example, a method comprising generating all the combinations of one or more structural units having substitutable sites and one or more connectors can be employed. For example, the generation of the basic molecular structures may be performed by the steps set out below.

In the step (A), the basic molecular skeleton itself may also be selected from one or more molecular skeletons generated by combination. For creating such molecular skeletons, for example, a method comprising preparing all the combinations of one or more structural units having substitutable sites and one or more connectors to connect between two structural units can be employed. For example, the generation of the basic molecular structures may be performed by the following steps:

(E) step of selecting one or more structural units from utilizable structural units;

(F) step of optionally adding conditions for use of each structural unit such as the maximum use in a molecular structure, whether or not adjacent use is acceptable, and whether or not the use is limited only at the end;

(G) step of selecting one or more connectors from utilizable connectors;

(H) determining the minimum and maximum numbers of structural units to be connected and generating all possible combinations of all of the structural units and the connectors selected in the above steps (E) and (G) (or when conditions for use are established for one or more structural units in the above step (F), generating all possible combinations satisfying the conditions) to generate one or more basic molecular skeletons.

The databases conventionally used or the database search method for identifying physiologically active compounds have been limited to those of existing and available compounds, and no compound database constructed in an artificial manner as described above has been applied to the databases search method. Therefore, the above compound database of the present invention is novel. Computer readable media for storing the databases is not particularly limited so long as it can surely store information of database and the information can be read when required. For example, computer readable media available to those skilled in the art such as magnetic tapes, hard disks, floppy disks, and CD ROM can be employed.

The method for constructing the compound database not limited to those mentioned above, and any database constructed by any method may fall within the scope of the present invention so long as it covers an the combinations of substitution sites selected from all the substitutable sites of the basic molecular skeleton and nominated substituents. The above-described method for preparing a compound database should be understood as an example, and it will be readily understood by those skilled in the art that appropriate alterations and modifications can be made depending on a purpose.

The second step of the method of the present invention comprises the step of retrieving compounds that meet the requirements necessary for exhibiting the physiological activity from the compound database mentioned above. This retrieval step is also performed by computers, and any algorithm may be used so long as it can be used as a method for retrieving compounds that meet the requirements necessary for exhibiting the physiological activity.

For example, compounds can be retrieved by selecting functional groups considered essential for exhibiting the desired physiological activity based on the chemical structure of a known medicament having the physiological activity, and superposing the basic molecular skeleton of the medicaments and three-dimensionally relative positions of the selected functional groups with the three-dimensional structural information of molecular structures stored in the compound database to judge similarity between the known medicament and the molecular structures. As such a superposing method, for example, programs such as ISIS-3D (MDL Information Systems, Inc.), UNITY (Tripos, Inc.), and Chem-X (Chemical Design, Ltd. ) are available for those skilled in the art.

As an alternative method for retrieval, when three-dimensional coordinates of the ligand-binding region of the target biopolymer are available, molecular structures that may bind to the biopolymer are preferably identified based on intermolecular interactions between the ligand-binding region and the molecular structures (for example, hydrogen bond, electrostatic interaction, van der Waals interaction and the like) using the program "ADAM&EVE". The details of this method are described in the specification of the Japanese Patent Application No. (Hei)6-267688/1994, and those skilled in the art can readily utilize this method by referring to the specification. The retrieval of molecular structures according to the program "ADAM&EVE" can be performed as follows.

Hydrogen-bonding category numbers, information for force-field energy calculation, and information for generating conformations are assigned to three-dimensional atomic coordinates of molecular structures stored in the above compound database. The hydrogen-bonding category numbers are identification numbers for functional groups capable of forming hydrogen bonds, and assigned to heteroatoms that directly participate in hydrogen bonds by the functional groups. By referring to the number, a geometric structure of the functional group and the nature of the hydrogen bond are characterized, and the positions of partner hydrogen-bonding atoms (dummy atoms) are instantly generated.

The information of force field energy calculation is numbers of atoms and the state of electrons given to each atom for calculating intramolecular and intermolecular interaction energies by means of molecular force field being used as atom type number and atomic charge. The information for generating conformations is used for generating different conformations by systematically varying torsion angles of rotatable bonds, including the initial and final values of the torsion angles and values of step angle. It includes, for one bond to be rotated, a set of four atomic numbers defying the torsion angle, and the initial and final values of the torsion angle and a step angle of rotation.

Physicochemical information about the ligand-binding region and one or more dummy atoms are prepared based on the three-dimensional atomic coordinates of the target biopolymer. The term "physicochemical information about the ligand-binding region" means various potentials affected by all atoms of the biopolymer inside the pocket to which a ligand can bind. The information includes hydrogen-bonding properties at grid point of a three-dimensional grid within the ligand-binding region hydrogen bond acceptor or hydrogen bond donor), and van der Waals interaction energies and electrostatic interaction energies generated between the biopolymer and probe atoms when the probe atoms are placed on the each of three-dimensional grid points. The dummy atoms can be generated at the positions of the heteroatoms in hydrogen bonding partners expected from hydrogen-bonding functional groups in the biopolymer.

Then, the most stable docking structure is estimated by generating possible docking structures by docking the trial molecular structure to the biopolymer while varying conformations of the molecular structure, and evaluating interaction energy between the target biopolymer and the trial molecular structure, based on the above hydrogen-bonding category number, the information for calculating force-field energies, and the information for generating conformations assigned to the three-dimensional atomic coordinates of the molecular structure in the compound database, and based on the above physicochemical information inside the ligand-binding region. The term "docking" embraces a concept which includes forming of a complex from a ligand compound molecule and a biopolymer, and/or the finding of a stable docking structure formed by both of them. The docking can generally be performed by using molecular models, interactive methods using computer and computer graphics technique, as well as by automatic docking methods.

The estimation of the most stable docking structures formed by the biopolymer and the trial molecular structure may be performed by, for example:
(1) covering all binding modes between the biopolymer and the molecular structure by covering all the combinations of correspondences between the dummy atoms and hydrogen-bonding heteroatoms in the trial molecular structure;
(2) simultaneously estimating possible hydrogen-bonding schemes between the biopolymer and the trial molecular structure and conformations of hydrogen-bonding part of the trial molecular structure by comparing the distances between dummy atoms with the distances between the corresponded hydrogen-bonding heteroatoms while systematically changing the conformations of the trial molecular structure; and
(3) obtaining docking structures comprising the biopolymer and the trial molecular structure by converting the entire atomic coordinates of the trial molecular structure to the coordinate system of the biopolymer for each hydrogen-bonding scheme and conformation obtained in the step (2) based on the correspondences between the hydrogen-bonding heteroatoms in the trial molecular structure and the dummy atoms.

In addition, the estimation may be performed by the following steps after the above step (2). By applying these steps, it is possible to select appropriate docking structures even when the number of conformations to be generated is reduced, and accurate stable docking structures can be obtained:
(3) optimizing the conformations of the trial molecular structure so that the positions of the hydrogen-bonding heteroatoms in the trial molecular structure are in accord with those of the corresponded dummy atoms while retaining the hydrogen-bonding scheme obtained in the step (2), and then excluding the conformations of the trial molecular structure having high intramolecular energies;
(4) obtaining a structure of docking structure comprising the biopolymer and the trial molecular structure by converting the entire atomic coordinates of the trial molecular structure to the coordinate system of the biopolymer for each conformation not excluded in the step (3) based on the correspondences between the hydrogen-bonding heteroatoms in the trial molar structure and the dummy atoms;
(5) excluding from the docking structures of hydrogen-bonding parts obtained in the step (4) the docking structures in which intramolecular energies of the hydrogen-bonding parts of the trial molecular structure and intermolecular energies between the biopolymer and the hydrogen-bonding parts of the trial molecular structure are high, and then carrying out structure optimizations of the remaining docking structures;
(6) obtaining new docking structures comprising the whole trial molecule structure by generating the conformations of non-hydrogen-bonding parts of the trial molecular structure for each docking structure obtained in the step (5); and
(7) excluding from the docking structures obtained in the step (6) the doing structures in which intramolecular energies of the whole structure of the trial molecule and intermolecular energies between the biopolymer and the trial molecular structure are high, and then carrying out structure optimizations of the remaining docking structures.

When the biopolymer and/or the trial molecular structure have complicated structures, for example, the following step may be utilized to accelerate the search for stable docking structures comprising the biopolymer and the trial molecular structure:
(1) covering all binding modes between the biopolymer and the trial molecular structure by covering all combinations of correspondences between the dummy atoms and hydrogen-bonding heteroatoms in the partial structure of the trial molecular structure;
(2) simultaneously estimating hydrogen-bonding schemes between the biopolymer and the trial molecular structure and conformations of the partial structure of the trial molecular structure by comparing the distances between dummy atoms with the distances between the corresponded hydrogen-bonding heteroatoms while systematically changing the conformations of the partial structure of the trial molecular structure;

(3) excluding correspondences of the dummy atoms and the hydrogen-bonding heteroatoms that provide impossible hydrogen-bonding schemes in the partial structure of the trial molecular structure, and hydrogen-bonding heteroatoms that cannot form any hydrogen-bond with the dummy atoms based on the hydrogen-bonding schemes and conformations obtained in the step (2), and covering favorable binding modes between the biopolymer and the trial molecular structure by covering all combinations of correspondences between dummy atoms and hydrogen-bonding heteroatoms in the whole structure of the trial molecular structure;

(4) simultaneously estimating possible hydrogen-bonding schemes between the biopolymer and the trial molecular structure and conformations of hydrogen bonding part of the trial molecular structure by comparing the distances between dummy atoms with the distances between hydrogen-bonding heteroatoms while systematically changing the conformations of the trial molecular structure; and (5) obtaining a structure of a docking structure comprising the biopolymer and the trial molecular structure by converting the entire atomic coordinates of the trial molecular structure to the coordinate system of the biopolymer or each hydrogen-bonding scheme and conformation obtained in the step (4) based on the correspondences between the hydrogen-bonding heteroatoms in the trial molecular structure and the dummy atoms.

In the above methods, the hydrogen-bonding functional groups include functional groups and atoms that can participate in the formations of hydrogen bonds. The term "hydrogen-bonding heteroatoms" means heteroatoms which exist in the hydrogen-bonding functional groups present in the trial molecular structures. The term "hydrogen-bonding part" means a partial structure of the trial molecular structure which comprises the hydrogen-bonding heteroatoms corresponding to dummy atoms, and the term "non-hydrogen-bonding part" means a partial structure other than the hydrogen-bonding part.

As a program for searching compound database utilizing three-dimensional structures of the ligand-binding site of the target biopolymers, "EUREKA" (the method for designing physiologically active compounds disclosed in PCT/JP96/03325, disclosure of the specification of this application is herein incorporated by reference) may also be utilized. The program "EUREKA" involves a method capable of identifying compounds that may bind to the biopolymer from databases based on structures of ligand molecules which has been confirmed or assumed to bind to the biopolymer and their binding modes to the biopolymer. For utilizing "EUREKA" in the method of the present invention, for example, when binding mode of a compound having a basic skeleton structure or a compound having a similar structure, used for the database construction, to the biopolymer is known or can be estimated, the whole or a part of such a structure can be used for the searching as a query structure.

In the database searching according to this method, the binding mode of the query molecule to the biopolymer and conformation thereof are assumed to be not changed in the compounds to be searched (trial molecules), and whether or not a trial molecule can form a stable docking structure with the biopolymer is determined solely by changing conformations of substituents not present in the query structure but present in the trial molecule. Criteria for the retrieval can be established as in the aforementioned program "ADAM&EVE". Because the search method utilizing "EUREKA" does not require to consider the binding mode of a part common to the query structure and the structures of the compounds in the database and the flexibility of conformation, extremely high speed search can be achieved. While this search method may sometimes be not suitable for searching of a database containing compounds whose basic skeletons themselves are diversified, it can be extremely suitably utilized for searching of compound database constructed by changing only types or positions of substituents on a few basic molecular skeletons.

Whether or not a molecular structure is acceptable as a ligand candidate is judged based on the value of interaction energy between the biopolymer and the trial molecular structure in the most stable docking structure searched by above mentioned methods. Then, by repeating the search of the most stable docking structure and the judgement of its acceptability as a ligand candidate compound for every molecular structure stored in the compound database, ligand candidate compounds which may bind to the target biopolymer can be identified from the compound database.

EXAMPLE

A preferred embodiment of the present invention utilizing the program "ADAM&EVE" for the second step will be explained more specifically with reference to a working example.

One or more basic molecular skeletons, which will be basic structures of molecular structures to be created are first selected for construction of compound databases. As the basic molecular skeletons, molecular skeletons of drugs, agricultural chemicals and the like already known to have the desired physiological activity can be used. For example, benzodiazepine skeleton, barbiturate skeleton, urea skeleton, phenothiazine skeleton, butyrophenone skeleton, xanthine skeleton, phenethylamine skeleton, morphine skeleton, prostaglandin skeleton, steroid skeleton, penicillin skeleton, cephalosporin skeleton, quinolonecarboxylic acid skeleton, tetracycline skeleton and other can be used. However, the skeletons are not limited to these examples, and any other structures known to those skilled in the art as skeletons of drugs, agricultural chemicals and other can be used. Among them, it is preferred to use molecular skeletons whose structural information such as three-dimensional coordinates are available as the basic molecular skeletons.

Then, in the step (B), one or more substitution sites to be introduced with substituents are selected from all substitutable sites existing on the basic molecular skeleton for each basic molecular skeleton. The step will be explained as to benzodiazepine skeleton represented by the following formula (I), for example, The diazepine ring as 7-membered ring has 6 substitutable sites ($R^1$–$R^6$, possibility of an N-oxide group at 4 position is ignored), and the benzene ring condensed with the diazepine ring has 4 substitutable sites ($R^7$–$R^{10}$). Accordingly, the benzodiazepine skeleton has 10 substitutable sites in total. When it is desired that substituents are introduced into all of these substitutable sites, all of $R^1$–$R^{10}$ may be selected as the substitution sites. When it is not desired that substituents are introduced into $R^7$, $R^9$ and $R^{10}$ on the benzene ring, for example, $R^1$–$R^6$ and $R^6$ can be selected as the substitution sites among the ten substitutable sites. For $R^7$, $R^9$ and $R^{10}$ not selected, hydrogen atoms can be applied, if necessary.

When the benzodiazepine skeleton represented by the formula (I) has a substituted or unsubstituted phenyl group as $R^6$, the basic molecular skeleton is represented as a skeleton of the formula (II), and one or more substitution sites to which substituents should be introduced can be selected from the substitutable site of $R^1$–$R^5$, $R^7$–$R^{10}$ and $R^{11}$–$R^{16}$. When various atoms are selected for the atoms constituting the rings of the benzodiazepine skeleton or a phenyl-substituted alkyl group is selected as $R^6$ in the skeleton represented by the formula (I), basic molecular structures can be created as combinations according to the formula (II). For example, combinations of basic molecular structure can be created by choosing X from $CR^2R^5$, $NR^2$, O and S; and choosing Y from $CR^4R^5$, $NR^4$, O and S; and choosing Z from a $C_{1-6}$ alkylene group, $NR^{16}$, O and S for combinations.

Then, utilizable substituents are selected. Examples of the substituents include, for example, a $C_1$–$C_{12}$ alkyl group, a $C_1$–$C_{12}$ alkoxy group, phenyl group, pyridyl group, carboxyl group, an alkyl ester group, hydroxyl group, carbonyl group (oxo group), a halogen atom, amino group, carbamoyl group, a hydroxyalkyl group, nitro group, sulfonic acid group and the like. However, the substituents are not limited to these examples, and any types of substituents can be selected.

For example, when a "$C_1$–$C_{12}$ alkyl group" is selected as a utilizable substituent, it is desirable that all of alkyl groups embraced within the "$C_1$–$C_{12}$ alkyl group" (straight-chain, branched-chain, and combinations thereof) are listed beforehand and stored as a substituent group. When pyridyl group is selected as a substiutent, for example, it is desirable to prepare a substituent group containing all of o-, m- and p-substitution position.

In the above step, the maximum number of substituents to be introduced can be decided, if necessary, for each of the selected substiuent (or the substituent groups). Examples of such limitation include, for example, where numbers of hydroxyl group to be introduced in the basic molecular skeleton to be created are 3 or less; or where numbers of phenyl group to be introduced in the basic molecular skeleton to be created are 2 or less, numbers of amino group are 4 or less, and numbers of $C_1$–$C_{12}$ alkyl group are 3 or less.

It is also possible to prepare correspondences of certain substitution sites and certain substituents (or substituent group), if necessary. For example, such correspondences can be prepared so that, when $R^1$–$R^5$ and $R^7$ are selected as the substitution sites in the benzodiazepine skeleton of the above formula (I), the substituent for $R^7$ is selected only from halogen atoms (a substituent group consisting of fluorine atom, chlorine atom, bromine atom and iodine atom). When a divalent or more valence of substituent such as oxo group (O=) is selected, it is desirable to prepare beforehand the correspondences of these substituents with substitutable substitution sites. For example, in the aforementioned benzodiazepine skeleton, two sites, $R^2$ together with $R^8$, and $R^4$ together with $R^5$, can be corresponded with oxo group as the substitutable sites. Alternatively, when oxo group is utilized, another basic molecular skeleton containing oxo group in the original basic molecular skeleton may be prepared.

An another example for the creation of basic molecular skeletons by combination includes the following combination:

AxAxAxA, AxAyAxA, AxAyAzA, ..
AxBxAxA, AxByAxA, AxByAzA, ..
AxBxCxA, AxByCxA, AxByCzA, ..
AxBxCxD, AxByCxD, AxByCzD, ...
BxAxAxA, BxAyAxA, BxAyAzA, ..
...

Structural units

A, B, C, D, ... =

-continued

Connectors x, y, z, ... =

Molecular structures based on combinations of structural units and connectors are first prepared by using four structural units (A–D) and three connectors (X–Z) to connect the structural units. Then, one or more units utilizable for each structural unit present in each molecular skeleton (e.g., in the above scheme, m-phenylene group to which $R^{20}$–$R^{23}$ bind, p-phenylene group to which $R^{24}$–$R^{27}$ bind, methylene group to which $R^{28}$ and $R^{29}$ bind, cyclohexandiyl group to which $R^{30}$–$R^{33}$ bind) and binding groups utilizable as the connectors (e.g., in the above scheme, amide group, or urea group) are selected. Basic molecular skeletons are then prepared by covering all combinations of the units and the binding groups.

Subsequently, all possible combinations of all the selected substitution sites and all the selected substituents (or substituent group) are prepared to create molecular structures in a number corresponding to the total number of the combinations. As to a substituent group, all possible combinations of all of the substitution sites and all components included in the substituent group should be prepared. When an upper limit is set for number of a substituent (or substituent group), and/or when correspondences between substituents (or substituent group) and substitution sites are prepared, all possible combinations that meet the requirements are prepared.

The number of the molecular structures to be generated is not particularly limited, however, it is preferred to prepare about several tens of thousands to several millions of molecular structures are prepared so that efficient and highly accurate searching can be performed by applying the database method. It is also possible to prepare about several tens to hundreds of thousands molecular structures utilizing typical substituents (or substituent group), carry out the second step (retrieval step) using a database containing these molecular structures to select substituents (or substituent group) required to exhibit the physiological activity, and further construct a database covering all combinations of such substituents (or substituent group) to perform the second step. A method comprising such repetition also fall within the scope of the present invention.

In order to use the program "ADAM&EVE" (Japanese Patent Application No. (Hei)6-267688/1994) as the retrieving method of the second step, three-dimensional structure information of the created molecular structures is stored in the compound database (S1). When three-dimensional coordinate information of the basic molecular skeleton can be utilized, three-dimensional coordinates of the created molecular structures can be calculated based on that three-dimensional information. When such three-dimensional coordinate information cannot be utilized, three-dimensional coordinates can be calculated by a method of, for example, CONCORD (TRIPOS Associates Inc.); CONVERTER (BIOSYM/MSI Inc.) and CORINA (Sadowski, J. and Gasteiger, J., Chem., Rev., 93, pp.2567–2581, 1993). As to steric structures represented by atomic coordinates of molecular structures, conformations are basically not required to be taken into account so long as geometric values such as bond distances and bond angles between the atoms are accurate. However, in order to calculate atomic charge of each atom in molecular structures as accurately as possible, it is preferred to input atomic coordinates of a structure relatively stable by itself.

Figure 1:
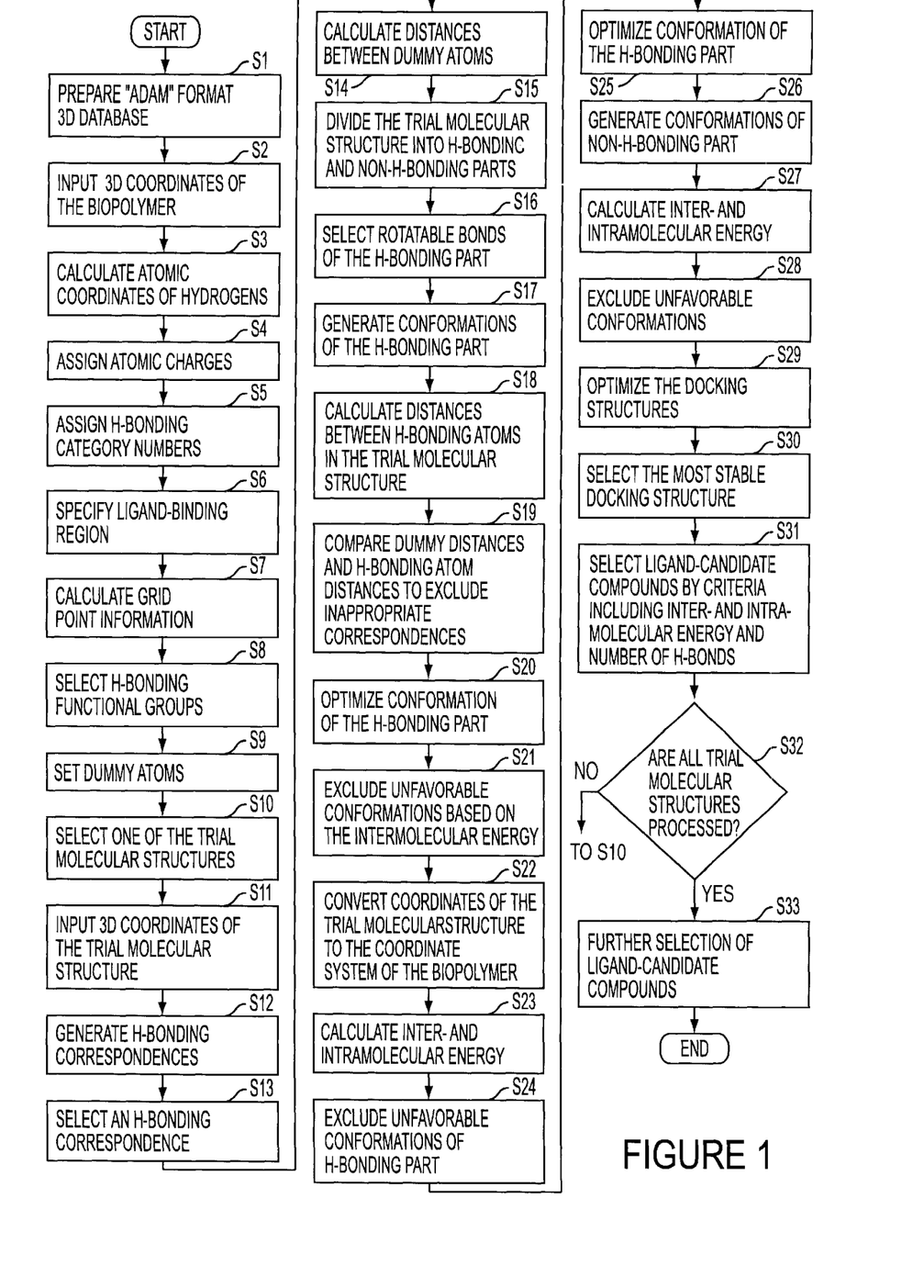
FIG. 1 shows a flowchart for the case using the program ADAM&EVE as the method of identifying ligand candidate compounds exhibiting physiological activity from a compound database. In the FIGURE, S represents each step.

A method according to the program ADAM&EVE (the method described in Japanese Patent Application No. (Hei) 6-267688/1994) will be specifically explained below, which method is for identifying molecular structures that may bind to the ligand binding site of the target biopolymer (ligand candidate molecular structures) based on the possibility of binding to the ligand binding site of the target biopolymer as a requirement for exhibiting the physiological activity from compound databases. In FIG. 1, the symbol "S" represents each step and the name "ADAM" represents the method for searching the most stable docking structure of a biopolymer and a ligand molecule disclosed in International Publication WO93/20525 (International Publication Date: Oct. 14, 1993). The disclosure of the International Publication WO93/20525 and the disclosure of the specification of the Japanese Patent Application No (Hei)6-267688/1994 are herein incorporated by reference.

The "ADAM" format three-dimensional database is first prepared for molecular structures stored in the compound database (S1). As the three-dimensional coordinates of the molecular structures, three-dimensional coordinates obtained by converting two-dimensional coordinates through force field calculation or those obtained from crystal structure databases for compounds having the basic molecular skeleton or those obtained by model building procedures based on energy calculation and other may be used. As regards three-dimensional structures defined by atomic coordinates of each molecular structure, conformations are basically not required to be taken into account so long as geometric values such as bond distances and bond angles between the atoms are accurate. However, in order to calculate atomic charge of each atom in the molecular structure as accurately as possible, it is preferred to input atomic coordinates of a structure relatively stable by itself.

After inputting the three-dimensional coordinates of the molecular structures, a three-dimensional database can be prepared automatically by adding hydrogen atoms if necessary, and assigning a force-field atom-type number to each atom, hydrogen-bonding category numbers to hydrogen-bonding heteroatoms, atomic charge to each atom, and modes of bond rotations (for example, information about covalent bonds to be rotated, values of initial and increment torsion angles of the rotation). The force-field atom-type number or each atom constituting the molecular structure can be assigned, for example, according to the numbering scheme of Weiner et al. (Weiner, S. J. et al, J. Am. Chem. Soc., 106, 1984, pp.765–784).

The hydrogen-bonding category numbers for hydrogen-bonding heteroatoms in the molecular structure can be assigned according to the following Table 1 (in the table, the numbers of the left column indicate the hydrogen-bonding category numbers). The atomic charge of each atom constituting the molecular structure can be calculated, for example, by the Gasteiger method or by molecular orbital calculation with MNDO, AM1 or other method in the MOPAC program. As to the scheme of bond rotation, it is preferred to chose a scheme of bond rotation in which all rotatable single bonds are systematically rotated with a given rotation-angle intervals of 60° to 120°.

TABLE 1

| | |
|---|---|
| 1 | $sp^2$ N in Primary Amines |
| 2 | $sp^3$ N in Primary Amines |
| 3 | $sp^3$ N in Ammonium Ions |
| 4 | $sp^2$ N in Amides |
| 5 | $sp^3$ N in Secondary Amides |
| 6 | N in Aromatic Groups |
| 7 | Protonated N in Aromatic Groups |
| 8 | N in Tertiary Amines |
| 9 | Protonated N in Tertiary Amines |
| 10 | O in Hydroxyls with Rotatable C—O bond |
| 11 | O in Ethers |
| 12 | O in Carbonyls |
| 13 | O in Carboxylate Anions |
| 14 | O in Carboxylic Acids |
| 15 | O in Phosphates |
| 16 | O in Water Molecules |
| 17 | S in Mercaptos |
| 18 | S in Thioethers |
| 19 | O in Hydroxyls with fixed hydrogen atom positions |

Then, the atom number and their atomic coordinates (except for atomic coordinates of hydrogen atoms) in the biopolymer are inputted (S2). As regards the atomic coordinates of the biopolymer, three-dimensional information obtained by X-ray crystallographic analyses of NMR analyses, information obtainable from the protein crystal structure database and other, or alternatively, atomic coordinates of a biopolymer model constructed on the basis of such information or the like may be used. The atomic coordinates of the biopolymer are preferably provided as a three-dimensional coordinate system. In addition, a cofactor that binds to the biopolymer and that structurally as well as functionally play important roles may be considered as a part of the biopolymer, and the atomic coordinates of the biopolymer in the bound state with the cofactor may be inputted to perform the successive steps. Examples of the cofactor include coenzymes, water molecules, metal ions and the like.

Following the above step, the atomic coordinates of the hydrogen atoms as components of amino acid residues in the biopolymer are generated (S3). In general, it is difficult to determine the positions of hydrogen atoms in biopolymers by experimental procedures such as X-ray crystallographic analyses or NMR analyses. In addition, the information about hydrogen atoms is also not available from protein crystal structure databases or the like. Therefore, it is necessary to calculate the atomic coordinates of the hydrogen atoms in amino acid residues on the basis of the structures of the amino acid residues present in the biopolymer. For hydrogen atoms whose atomic coordinates cannot be uniquely determined as they bind to rotatable amino acid residues, their atomic coordinates are preferably calculated on the assumption that they exist at trans positions.

Subsequently, atomic charges are appended to the atoms constituting amino acid residues present in the biopolymer (S4), and then hydrogen-bonding category numbers are assigned to the heteroatoms in hydrogen-bonding functional groups present in the biopolymer (S5). As the values of the atomic charges, reported values calculated for each amino acid, for example, values reported by Weiner et al. can be used (Weiner, S. J., et al., J. Am. Chem. Soc., 106, 1984, pp. 765–784). The hydrogen-bonding category numbers can be assigned according to the above Table 1.

A ligand-binding region is then specified (S6). As the ligand-binding region, a region containing any site of the biopolymer, preferably a rectangular box region, can be specified. Depending on purposes, the ligand-binding pocket and its surrounding region of the biopolymer can be specified. If desired, a region contain a site in the biopolymer to which a different molecule such as an effector binds can also be specified. The term "ligand-binding region" means a cavity on the concaved surface of the biopolymer to which a ligand molecule such as a substrate or an inhibitor binds. For assigning the range of the ligand-binding region, a part of the functions of the program "GREEN" can be used (Tomioka, N. et al., Journal of Computer-Aided Molecular Design, 1, 1987, pp197–210).

Three-dimensional grid points are generated inside the ligand-binding region specified in the step S6, and for each three-dimensional grid point, an address number is assigned and grid point information is calculated (S7). The term "three-dimensional grid points" means the points on the three-dimensional lattice generated at a certain regular intervals within the ligand-binding region in the biopolymer. The meaning of "grid point information" includes local physicochemical character in the ligand-binding region, on the assumption that probe atoms are placed on each three-dimensional grid point, such as van der Waals interaction energies and electrostatic interaction energies arisen between the biopolymer and probe atoms, and hydrogen-binding properties. By using the grid point information on the three-dimensional grid points, it becomes possible to accelerate approximate calculations of the intermolecular interactions between the biopolymer and the molecular structures in the compound database to be carried out in the successive steps. In addition, reasonable determination of the positions of the dummy atoms, which is provided in the following steps, can be achieved. As a result, a docking model comprising the biopolymer and the molecular structure can be entirely searched in a short time.

The three-dimensional grid points may be generated at intervals of 0.3–2.0 angstroms, preferably 0.3–0.5 angstroms in the region specified in the step S6. As the probe atoms, all sorts of atoms contained in molecular structures in the compound database may preferably be included. The van der Waals interaction energy that acts between each probe atom placed on a three-dimensional grid point and all atoms in the biopolymer can be calculated according to a conventional atom-pair type calculation using an empirical potential function. As the empirical potential function, the Lennard-Jones type function represented by the following equation can be used.

$$G_{vdw,j} = \sum_{j} (A/r_{ij}^{12} - B/r_{ij}^{6})$$

In the formula, symbol "i" is a sequential number representing a probe atom; and symbol "j" is a sequential number for the biopolymer atoms. Symbols "A" and "B" are parameters for determining potential curves for each atom pair. Symbol "$r_{ij}$" is an inter-atomic distance between the i-th probe atom and the j-th atom in the biopolymer. As the parameters "A" and "B," the values reported by Weiner et al. can be used (Weiner et al., J. Am. Chem. Soc., 106, 1984, pp.765–784).

The van der Waals interaction energy between the molecular structure and the biopolymer, when the molecular structure is placed on the three-dimensional grid points, can be calculated by the following equation:

$$E_{vdw} = \sum_{m=1}^{N} G_{vdw,m_0}$$

wherein "m" is the sequential number for each atom in the molecular structure; N is the total number of atoms in the molecular structure; and "$m_0$" is the sequential number of the three-dimensional grid point that is closest to the m-th atom.

The electrostatic interaction energy that generates between each probe atom placed on each three-dimensional grid point and the biopolymer can be calculated by the following equation:

$$G_{ele,i} = \sum_{j} Kq_j / \varepsilon r_{ij}$$

wherein symbols "i," "j," and "$r_{ij}$" are the same as those defined above; "$q_j$" is the atomic charge of the j-th atom in the biopolymer; "K" is a constant for converting an energy unit; and "e" is a dielectric constant. As the dielectric constant, a fixed value may be used, or alternatively, it is preferably to use a value depending on $r_{ij}$, as proposed by Warshel et al. (Warshel, A. J. Phys. Chem, 83, 1979, pp. 1640–1652).

The electrostatic interaction energy between the molecular structure and the biopolymer, when the molecular structure is placed on the three-dimensional grid points, can be calculated by the following equation:

$$E_{elc} = \sum_{m=1}^{N} q_m G_{elc,m_0}$$

wherein m, N and $m_0$ are as defined above.

Then, information representing hydrogen-bonding property at each three-dimensional grid point (hydrogen-bonding grid point information) is added. This information indicates that either hydrogen-donor or hydrogen-acceptor atom can form a hydrogen bond with the hydrogen-bonding functional group in the biopolymer if the atom is placed on the three-dimensional grid point, or alternatively, that both hydrogen-donor and hydrogen-acceptor atom can (or cannot) form a hydrogen bond with the hydrogen-bonding functional group in the biopolymer if the atom is placed on the three-dimensional grid point. For example, the hydrogen-bonding information of three-dimensional grid points can be expressed by assigning number 1 for a three-dimensional grid point as a hydrogen-bond acceptor, number 2 for a three-dimensional grid point as a hydrogen-bond donor, number 8 on a three-dimensional grid having both properties, and number 0 on a three-dimensional grid having no hydrogen-bonding property.

The hydrogen-bonding grid point information can be obtained as set forth below. If the distance "DP" between a three-dimensional grid point Y and a hydrogen-donating heteroatom "D" in the biopolymer is within a range that allows for the formation of a hydrogen bond (e.g., 2.5–3.1 Å), and if the angle <DHP made by the three-dimensional grid point "P", hydrogen "H," and atom "D" is within a range that allows for the formation of a hydrogen bond (e.g., more than 30°), the three-dimensional grid point is determined to have the property of hydrogen-bond acceptor. Similarly, if the distance "PA" between the three-dimensional grid point "P" and hydrogen-accepting heteroatom "A" in the biopolymer is within a range that allows for the formation of a hydrogen bond and if the angle <ALP which is made by the three-dimensional grid point "P," a lone-pair electron "L," and the hydrogen-accepting atom "A" is within a range that allows or the formation of a hydrogen bond, the three-dimensional grid point is determined to have the property of hydrogen-bond acceptor. If a three-dimensional grid point is proved to have neither the property of hydrogen-bond donor nor hydrogen-bond acceptor, the point is assumed to have no hydrogen-bonding property.

Hydrogen-bonding functional groups that are expected to form hydrogen bonds with the molecular structure are then selected from hydrogen-bonding functional groups present in the region of the biopolymer specified in the step S6 (S8). If a lot of hydrogen-bonding functional groups are present, they can be selected depending on the degree of importance. Furthermore, one or more dummy atoms are set to each hydrogen-bonding functional group selected in step S8 based on the three-dimensional grid point information calculated in S7 (S9).

In this step, a region in which a hydrogen-bond can be formed with each hydrogen-bonding functional group selected in step S8 (hydrogen-bonding region) is first determined based on the hydrogen-bonding grid point information calculated in step S7, and then a dummy atom is placed at the center of the hydrogen-bonding region comprising appropriate numbers of three-dimensional grid points, e.g., 5–20. The dummy atom is located within the hydrogen-bonding region and outside the van der Waals radii of other atoms. The hydrogen-bonding region is defined as a mass of three-dimensional grid points that are neighboring to each other and have the same hydrogen-bonding properties. It should be noted that two or more dummy atoms may sometimes be placed from a single hydrogen-bonding functional group, or in contrast, no dummy atom may be generated. If a large number of dummy atoms is generated, it is preferred to reduce the number to 10 or less, more preferably 5 to 10, by selecting dummy atoms present in a bottom of the cavity of the ligand-bonding region considering the importance. To each dummy atom, the same hydrogen-bond property is assigned as that of the three-dimensional grid point to which the dummy atom belongs.

Then, one of the molecular structures stored in the compound database is selected (S10) and then three-dimensional coordinates, hydrogen-bonding category numbers, information for molecular force-field calculation, and information for conformation generation are read from the "ADAM" format database prepared in S1 (S11). Then, correspondences are made combinatorially between the dummy atoms and the hydrogen-bonding heteroatoms in the molecular structure (S12). If the number of dummy atoms is "m" and the number of hydrogen-bonding heteroatoms in the molecular structure is "n", the number of the correspondences (combination) represented by N(i), in which number of hydrogen-bonds formed is "i", is mPi×nCi wherein symbol "P" represents permutations and symbol "C" represents combinations. It is preferred to generate all possible combinations of the dummy atoms and the hydrogen-binding heteroatoms in the molecular structure.

Then, for all "i"s that satisfy the relationship $l_{min} < i < l_{max}$, the steps S12–S39 are repeated. As a result, a total of $$\sum_{i=1_{\min}}^{I_{\max}} N(i)$$

sets of correspondences of dummy atoms and hydrogen-bonding heteroatoms in the molecular structure are generated. By these procedures, all possible combinations of the hydrogen-bonds formed between the biopolymer and the molecular structure are generated, and thereby all the binding modes between the molecular structure and the biopolymer can be searched systematically and efficiently. It is preferred to set $l_{min}$ as the smaller number of the dummy atoms or the hydrogen-bonding heteroatoms, and set as $I_{max}$ the larger number of the dummy atoms or the hydrogen-bonding heteroatoms.

More specifically, one of the combinations of the dummy atoms and the hydrogen-binding heteroatoms in the molecular structure, which are corresponded in S12, is selected (S13). In this step, correspondences in which the hydrogen-bonding properties of the dummy atoms do not match those of the hydrogen-bonding heteroatoms in the molecular structure are not selected. Then, interatomic distances are calculated or all pairs of dummy atoms contained in the correspondence selected in S13 (S14). If both the number of dummy atoms and the number of hydrogen-bonding heteroatoms in the molecular structure are 1, the process jumps to step S22 skipping steps S14–S21 and then jumps to step S26 skipping steps S23–S25. If either of the number of dummy atoms or the number of hydrogen-bonding heteroatoms in the molecular structure is 1, the process jumps to step S22 skipping steps S14–S21.

Then, the molecular structure is divided into a hydrogen-bonding part and a non-hydrogen-bonding part (S15), and rotatable bonds and their rotation modes in the hydrogen-bonding part divided in step S15 are select (S16). Then, conformations of the molecular structure are generated successively by rotating the bonds selected in step S16 according to the rotation modes inputted in the three-dimensional "ADAM" format database prepared in S1 (S17). For each generated conformation, subsequent steps S1–S29 are performed.

These steps will be detailed below. For each conformation generated in step S17, interatomic distances are calculated for all pairs of hydrogen-bonding heteroatoms in the molecular structure contained in the combination selected in step S13 (S18). If the value of "F", which is the sum of the squares of the differences between he interatomic distances of dummy atoms obtained in S14 and the corresponded hydrogen-bonding heteroatoms of the molecular structure obtained in S38, is above the given range, such hydrogen-bonding combinations and conformations are excluded (S19). That is, when F is calculated by the following equation:

$$F = \sum_{i=1}^{n(n-1)/2} (r_{li} - r_{di})^2$$

hydrogen-bonding correspondences are excluded wherein $k_n < F < k_n'$ (in the formula, "n" is the number of hydrogen bonds; "$r_{di}$" is the i-th distance between dummy atoms; and "$r_{li}$" is the i-th distance between hydrogen-bonding heteroatoms in the molecular structure; "$k_n$" is the lower limit of F; and "$k_n$" is the upper limit of F). The value of $k_n$ is preferably 0.6–0.8 and that of $K_n'$ is preferably 1.2–1.4. In this step, possible hydrogen-bonding schemes between the biopolymer and the molecular structure and possible conformations of the ligand molecule can be searched efficiently and thoroughly.

Then, for the hydrogen-bonding correspondences and conformations not excluded in step S19, the conformation of the hydrogen-bonding part of the molecular structure is otpimized so as to minimize the value of F (S20). In this step, the conformation of the molecular structure is corrected so that the biopolymer and the molecular structure can form stable hydrogen bonds. The conformation of the hydrogen-bonding part of the molecular structure can be optimized by minimizing the value of F using the Fletcher-Powell methed (Fletcher, R., Powell, M. J. D., Computer J., 6, 1968, p.163), treating the torsion angles of the rotatable bonds as variables that are present in the hydrogen-bonding part of the molecular structure.

Then, the intramolecular energy is calculated for the hydrogen-bonding part of the molecular structure optimized in step S20, and the conformations with intramolecular energies higher than a given threshold are excluded (S21). For example, when the intramolecular energy of the hydrogen-bonding part of the molecular structure is calculated by using the molecular force field of AMBER 4.0, conformations with an intramolecular energy of more than 100 kcal/mol are preferably excluded. The atomic coordinates of the molecular structure is then converted to the coordinate system of the biopolymer so that the coordinates of the hydrogen-bonding heteroatoms in the molecular structure in the conformation obtained in step S21 coincide with those of the corresponded dummy atoms (S22). The Kabsh's method of least squares can be used for this step (Kabsh, W., Acta Cryst., A32, 1976, p.922; Kabsh W., Acta Cryst, A34, 1978, p.827). By these procedures, possible hydrogen-bonding schemes and the conformations of the hydrogen-bonding part of the molecular structure can be estimated roughly at the same time.

Following the above step, the intermolecular interaction energy between the biopolymer and the hydrogen-bonding part of the molecular structure (the sum of a van der Waals interaction energy and electrostatic interaction energy) and the intramolecular energy of the hydrogen-bonding part of the molecular structure are calculated (S23). The intermolecular interaction energy between the biopolymer and the hydrogen-bonding part of the molecular structure $E_{inter}$ can be calculated by the following equation:

$$E_{inter} = \sum_k [G_{vdw}(k) + G_{clc}(k) \cdot q_k]$$

wherein "qk" is the atomic charge of the atom k, by using $G_{vdw}(k)$ as the van der Waals interaction energy and $G_{clc}(k)$ as the electrostatic interaction energies based on the grid point information at the grid point closest to the atom "k" in the molecular structure.

The intramolecular energy of the hydrogen-bonding part of the molecular structure $Ei_{intrn}$ can be calculated by known methods. For example, $E_{intrn}$ can be calculated by the following equation using a reported force field such as AMBER 4.0:

$$E_{intro} = \sum_{dihedralys} \sum_n \frac{V_n}{2}[1 + \cos(n\Phi - \gamma)] + \sum_{i<j}(A_{ij}/R_{ij}^{12} - B_{ij}R_{ij}^6) + \sum_{i<j}(q_i q_j/\varepsilon R_{ij})$$

wherein "$V_n$" is a constant provided for force-field atom types of four atoms constituting a torsion angle; "n" is a constant representing the symmetry of the torsion-angle potential; Φ is a torsion angle, γ is the phase of the torsion-angle potential (provided or force-field atom types of four atoms constituting a torsion angle); "$A_{ij}$" and "$B_{ij}$" are constants for a pair of force-field atom types of the i-th and j-th atoms in the molecular structure; "$R_{ij}$" is the distance between the i-th and j-th atoms; $q_i$ is the atomic charge on the i-th atom in the molecular structure; $q_j$ is the atomic charge on the j-th atom in the molecular structure, and ε is a dielectric constant.

Conformations of the molecular structure are excluded if the sum of the intermolecular interaction energy and intramolecular energy as calculated in step S28 is higher than a given threshold (S24). For example, conformations in which the sum of these energies is higher than 10 kcal/mol per 100 dalton of molecular weight may preferably be excluded. Then, the structure of the hydrogen-bonding part of the molecular structure is optimized if it was not excluded in step S24 (S25). The structures of the hydrogen-bonding part of the molecular structure can be optimized by calculation for structural optimization to optimize the torsion angles of the hydrogen-bonding part of the molecular structure as well as the relative location and orientation of the molecular structure.

For example, the structure of the hydrogen-bonding part of the molecular structure can be optimized by the Powell method (Press, W. H., Flannery, B. P., Teukolsky, S. A., Vitterling, W. T., "Numerical Recipes in C", Cambridge University Press, Cambridge, 1989) or the like, so that the total energy $E_{total}$ calculated by the following formula is minimized:

$$E_{total} = E_{inter} + E_{intra} + Whb \cdot Nhb \cdot Chb$$

wherein $E_{inter}$ and $E_{intra}$ are the same as those defined above; "Whb" is a weight; "Nhb" is the number of hydrogen-bonds; and "Chb" is a constant energy value assigned for one hydrogen-bond (e.g., 2.5 kcal/mol).

Then, conformations of the molecular structures are successively generated by rotating the rotatable bonds in the non-hydrogen-bonding part of the molecular structure according to the rotation mode inputted in the "ADAM" format three-dimensional database prepared in S1 (S26), and steps S27–S30 are repeated for each generated conformation. Specifically, the intermolecular interaction energy between the biopolymer and the molecular structure and the intramolecular energy of the molar structure are calculated (S27), and conformations of the molecular structure are excluded if the sum of the intermolecular interaction energy and intramolecular energy as calculated in S27 is higher than a given threshold (S28). The entire structure of the molecular structure having conformations not excluded in step S28 are then optimized (S29), and the energies are calculated for docking structures of the biopolymer and the molecular structure obtained by S29, and the most stable docking structure with the minimum energy is selected (S30).

The intermolecular interaction energy and intramolecular energy can be calculated in same manner as S23, provided that energies should be calculated for the whole structure of the molecular structure in S27, whereas energies are calculated only for the hydrogen-bonding part of the molecular structure in S23. As the upper limit for the sum of these energies, for example, 10 kcal/mol per 100 dalton of molecular weight can be used. Through this step, stable docking structures comprising the biopolymer and the molecular structure as well as active conformations of the molecular structure can be obtained. The optimization of the molecular structure can be carried out in the same manner as S25, provided that the optimization should be performed for the whole structure of the molecular structure in S29, whereas the optimization is directed only to the hydrogen-bonding part of the molecular structure in S25.

Whether or not the molecular structure should be selected as a ligand-candidate compound is decided based on all or a part of the given criteria including the intermolecular interaction energy between the biopolymer and the molecular structure, the intramolecular energy of the molecular structure, the number of hydrogen bonds, the number of rings and others, which is evaluated in the most stable docking structure obtained in S30 (S31). Examples of the intermolecular interaction energy include electrostatic interaction energy, van der Waals interaction, hydrogen bond energy, and the sum of them. For example, a molecular structure with the sum of the electrostatic and van der Waals interaction energies below –2 kcal/mol per molecular weight of 100 dalton can be selected as a ligand-candidate compound. Then, judgement is performed whether or not all of the molecular structures have been subjected to the selection (S32), and if not all of the molecular structures have been subjected to the selection, the steps of S10–S31 are repeated by returning to the step S10, and if the selection has been completed, the process proceeds to the step of S33.

More promising ligand-candidate compounds are farther selected from the ligand-candidate compounds selected in S31 (S33). Prior to the further selection, it is convenient to decide another criteria for the section by referring to a list of information about the ligand-candidate compounds in their most stable docking structures, e.g., the intermolecular interaction energy between the biopolymer and the molecular structure, the intramolecular energy of the molecular structure, the number of hydrogen bonds, and the number of rings and others. For example, a further selection is preferably carried out using a criteria comprised of the number of hydrogen bonds that are formed between the biopolymer and the ligand-candidate compound, the intermolecular interaction energy between the biopolymer and the ligand-candidate compound, and the number of atoms.

Examples of the intermolecular interaction energy include electrostatic interaction energy, van der Waals interaction, and the sum of them. For example, molecular structures with the sum of the electrostatic and van der Waals interaction energies below –8 kcal/mol per molecular weight of 100 dalton are preferably selected as ligand-candidate molecular structures. Although arbitrary number can be specified as a criterion of the number of hydrogen bonds depending on the nature of the biopolymer, it is desirable to apply a number of, for example, 2 or more, and more preferably 3 or more. The number of atoms may also be arbitrarily chosen, however, the number of, for example, 20 or more, preferably in the range of 20 to 40 can be specified.

If too many dummy atoms are generated from the biopolymer, or if the molecular structure has rather high conformational flexibility or has a lot of heteroatoms, information about the molecular structure is inputted according to the step S9, and then steps S13–S25 are carried out for a partial structure of the molecular structure and preserve information about correspondences of dummy atoms and hydrogen-bonding heteroatoms of the molecular structure that provide impossible hydrogen-bonding schemes and hydrogen-bonding heteroatoms that cannot form hydrogen bond with any dummy atom in the partial structure. Although the partial structure of the molecular structure can be arbitrarily specified without any structural restrictions, a partial structure containing at least three hydrogen-bonding functional groups is preferred. Presence or absence of conformational flexibility in the partial structure may be disregarded.

Subsequent to the above step, the steps of S13–S33 are performed for the whole structure of the molecular structure, excluding, from the set of correspondences prepared in the step S12, the correspondences containing the hydrogen-bonding heteroatoms and the correspondences of dummy atoms and hydrogen-bonding heteroatoms preserved in the aforementioned step. As a result, the number of the correspondences and conformations to be examined can be reduced, thereby time for structural searching for stable docking structure of the biopolymer and the molecular structure be greatly shortened (this method is sometimes referred to as the "Pre-Pruning method (PP method)"). The PP method is based on the assumption that any hydrogen-bonding schemes and ligand conformations that are impossible in the partial structure of the molecular structure are also impossible in the whole structure of the molecular structure. By applying the PP method, the time for the search can be remarkably shortened without affecting the accuracy and reliability of the resulted docking structure of the biopolymer and the molecular structure.

Industrial Applicability

According to the present invention, physiologically active compounds useful as drugs, agricultural chemicals and the like can be efficiently created. Because the database used for the method of the present invention contains an extremely large number of not biased molecular structures, the method enables to select an optimal molecular structure having the maximum physiological activity by a single retrieving process.

What is claimed is:

1. A method for creating physiologically active compounds using computers, comprising:
   (1) generating a compound database storing molecular structures covering all the combinations of one or more substitution sites selected from substitutable sites existing on a basic molecular skeleton and utilizable substituents; and
   (2) extracting molecular structures satisfying the requirements for exhibiting the physiological activity from the compound database.

2. The method of claim 1 wherein a molecular skeleton of known ligand having the desired biological activity or a molecular skeleton analogous thereto is used as the basic molecular skeleton.

3. The method of claim 1 wherein one or more molecular skeletons of ligand candidates generated by the automatic structure construction method or molecular skeletons analogous thereto are used as the basic molecular skeleton.

4. The method of claim 1 wherein one or more molecular skeletons of ligand candidates selected from a compound database containing compounds with variety of molecular skeletons by use of the program "ADAM&EVE" or molecular skeletons analogous thereto are used as the basic molecular skeleton.

5. The method of claim 1 wherein two or more basic molecular skeletons generated by combination are used.

6. The method of claim 5 wherein the generation of the basic molecular skeletons by the combination is carried out by a method comprising generating all the combinations of one or more structural units having substitutable sites and one or more connectors.

7. The method of claim 6 wherein the generation of basic molecular skeletons by combination is carried out by a method comprising the following:
   (E) selecting one or more structural units from all utilizable structural units;
   (F) optionally adding conditions for using each structural unit;
   (G) selecting one or more connectors from all utilizable connectors; and
   (H) determining the maximum and minimum numbers of structural units to be connected and generating all possible combinations from all structural units and all connectors selected in (E) and
   (G), or when conditions for using the units are established in (F), generating all possible combinations satisfying the conditions, to create one or more basic molecular skeletons.

8. The method of claim 1 wherein the retrieval (2) is carried out by a method comprising extracting molecular structures capable of binding to the target biopolymer based on interaction energy between the ligand-binding region of the biopolymer and the molecular structures.

9. The method of claim 8 wherein the retrieval process (2) is carried out by a method comprising estimating the most stable docking structure of the biopolymer and a compound taking into account the degrees of freedom for binding modes with the biopolymer and conformations of the compound.

10. The method of claim 1 wherein the retrieval process (2) is carried out by a method comprising extracting molecular structures capable of binding to the biopolymer based on the structure and binding mode to the biopolymer of a ligand molecule whose binding to the biopolymer is confirmed or assumed.

11. The method of claim 1 wherein the retrieval process (2) is carried out by a method of selecting lead candidate compounds capable of binding to the receptor biopolymer from a database containing information at least atom type of each atom and covalent bond schemes in compounds by using computers, which comprises selecting lead candidate compounds by matching one or more query molecules capable of binding to the biopolymer with compounds stored in a database based on information about atom types and covalent bond schemes of the query molecules.

12. The method of claim 1 wherein the retrieval process (2) is carried out by a method comprising judging similarity with a compound confirmed or assumed to have the desired biological activity based on the molecular structure of the compound or arrangement of functional groups in the compound.

13. A three-dimensional database used for a method for creating physiologically active compounds by database search methods using computers, which database stores molecular structures covering all the combinations of one or more substitution site selected from all substitutable sites existing on a basic molecular skeleton and utilizable substituents.

14. The database of claim 13 which is constructed by using the molecular skeleton of a known ligand having the desired biological activity or a molecular skeleton analogous thereto as the basic molecular skeleton.

15. The database of claim 13 which is constructed by using the molecular skeleton of a ligand candidate generated by the automatic structure construction method or a molecular skeleton analogous thereto as the basic molecular skeleton.

16. The database of claim 13 which is constructed by using the molecular skeleton of a ligand candidate selected from a compound database by use of the program "ADAM&EVE" or a molecular skeleton analogous thereto as the basic molecular skeleton.

17. The database of claim 13 which is constructed by using two or more molecular skeletons generated by combination.

18. A computer readable media storing a database of claim 13.

* * * * *